United States Patent
Kruglick et al.

(10) Patent No.: US 9,295,409 B2
(45) Date of Patent: Mar. 29, 2016

(54) SENSING OF GASEOUS LEAKAGE INTO BODY FOR EARLY DETECTION OF COLORECTAL ANASTOMOTIC LEAKAGE

(75) Inventors: Lewis Kruglick, Poway, CA (US); Ezekiel Kruglick, Poway, CA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 624 days.

(21) Appl. No.: 13/640,283

(22) PCT Filed: Apr. 27, 2012

(86) PCT No.: PCT/US2012/035632
§ 371 (c)(1),
(2), (4) Date: Oct. 9, 2012

(87) PCT Pub. No.: WO2013/162611
PCT Pub. Date: Oct. 31, 2013

(65) Prior Publication Data
US 2013/0289367 A1    Oct. 31, 2013

(51) Int. Cl.
*A61B 5/02* (2006.01)
*A61B 5/07* (2006.01)
(Continued)

(52) U.S. Cl.
CPC .................. *A61B 5/07* (2013.01); *A61B 5/0031* (2013.01); *A61B 5/076* (2013.01); *A61B 5/1468* (2013.01); *A61B 5/4255* (2013.01)

(58) Field of Classification Search
CPC .............. A61B 1/00; A61B 1/07; A61B 5/42; A61B 5/4222; A61B 5/4255; A61B 5/07; A61B 5/0031; A61B 5/1468; A61B 5/076
USPC .................. 600/301, 302, 343, 345, 364, 373
See application file for complete search history.

(56) References Cited

U.S. PATENT DOCUMENTS 4,458,242 A * 7/1984 Kusanagi et al. ............. 340/634
4,671,852 A    6/1987 Pyke
(Continued)

FOREIGN PATENT DOCUMENTS

WO        2007008057 A1    1/2007
WO    WO 2007008057 A1 *    1/2007

OTHER PUBLICATIONS

Dafina Tanase et al., Tissue-Viability Monitoring USing an Oxygen-Tension Sensor, 2008, Spinger-Verlag Berlin Heidelberg, pp. 109-122.*
(Continued)

*Primary Examiner* — Navin Natnithithadha
*Assistant Examiner* — Eric Messersmith
(74) *Attorney, Agent, or Firm* — Turk IP Law, LLC

(57) ABSTRACT

Technologies are generally described for a system for detecting the presence of gas in the intraperitoneal space of the abdominal cavity and indicating anastomotic leakage. A sensing device may be implanted inside the abdominal cavity of a body near the location of an anastomosis. The sensing device may utilize a sensor configured to detect gas presence and measure the concentrations of gases, including hydrogen sulfide and/or methane, within the intraperitoneal space. The sensing device may be configured to transmit gas detection information to an external wireless communication device, and the wireless communication device may be configured to generate an alert if a gas concentration level rises above a predetermined acceptable level. The wireless communication device may also be configured to transmit gas detection information to an external monitoring system for performing statistical analysis on the gas detection information for generating more accurate data and more accurately indicating potential anastomotic leakage.

11 Claims, 7 Drawing Sheets

(51) Int. Cl.
*A61B 5/00* (2006.01)
*A61B 5/1468* (2006.01)

(56) References Cited

U.S. PATENT DOCUMENTS

| | | | | |
|---|---|---|---|---|
| 4,729,824 | A * | 3/1988 | Giner | 204/415 |
| 4,947,104 | A * | 8/1990 | Pyke | 324/71.5 |
| 5,183,549 | A * | 2/1993 | Joseph et al. | 204/415 |
| 5,376,255 | A * | 12/1994 | Gumbrecht et al. | 204/426 |
| 2004/0176685 | A1* | 9/2004 | Takizawa et al. | 600/424 |
| 2006/0217637 | A1 | 9/2006 | Leiboff et al. | |
| 2009/0187087 | A1* | 7/2009 | Turcott | 600/328 |
| 2013/0096399 | A1* | 4/2013 | Scalici et al. | 600/309 |
| 2013/0150685 | A1* | 6/2013 | Toth | A61B 5/0059 600/302 |

OTHER PUBLICATIONS

J.B. Vortius et al., Soluble Gas Tight Capsules for Use in Surgical Quality Testing, 2009, Springer-Verlag Berlin Heidelberg 2009, pp. 895-898.*

International Preliminary Report on Patentability for PCT/US2012/035632 filed Apr. 27, 2012, mailed on Nov. 6, 2014, issued Oct. 28, 2014.

Electronic nose, From Wikipedia, the free encyclopedia, http://en.wikipedia.org/wiki/Electronic_nose Oct. 8, 2012, 6 pages.

Smith et al., Stability, sensitivity and selectivity of tungsten trioxide films for sensing applications. Sensors and Actuators B, 13/14 (1993), pp. 264-268.

The JPL Electric Nose (ENose) hltp:/lenose.jpl.nasa.gowpublicalionsiPosttr.gif[101812012 I 0:57:31 PM] 1 page.

Ruokamo et al., "H2S response of WO3 thin-film sensors manufactured by silicon processing technology," Sensors and Actuators B: Chemical 19, No. 1-3 (1994): 486-488.

Kruglick et al., "CMOS 3-axis accelerometers with integrated amplifier," in Micro Electro Mechanical Systems, 1998. MEMS 98. Proceedings., The Eleventh Annual International Workshop on (IEEE, 1998), 631-636.

Bult et al "Low-Power Systems for Wireless Microsensors", International Symposium on Low Power Electronics and Design, pp. 17-21, Aug. 1996.

Wireless Sensor Networks—Dust Networks, Linear Technology, http://www.linear.com/products/wireless_sensor_networks[Oct. 8, 2012 11:01:49 PM].

Microbattery.com, Sony Lithium Batteries, http://www.microbattery.com/tech-sony-lithium.htm[Oct. 8, 2012 11:02:29 PM].

International Search Report and Written Opinion PCT/US/12/35632 Filed on Apr. 27, 2012, mailed Jul. 6, 2012.

Collins et al., "Development of a technique for the in vivo assessment of flatulence in dogs," American Journal of Veterinary Research 62, No. 7 (2001): 1014-1019. Pub med.

GUT An International Journal of Gastroenterology and Hepatology, An international peer-reviewed journal for health professionals and researchers in gastroenterology & hepatology, http://gut.bmj.com/ [Oct. 8, 2012 11:47:40 PM].

Welcome to the JPL Electronic Nose! A Brief Introduction . . . http://enose.jpl.nasa.gov/; NASA Jet Propulsion Laboratory California Institute of Technology, http://enose.jpl.nasa.gov/ Oct. 8, 2012.

Tang, Early detection of anastomotic leakage using oxygen and carbon dioxide sensor', Master of Science thesis, Delft University of Technology, Mar. 2011 pp. 4-6; p. 11, section 2.2; p. 27, section 3.1; p. 51, section 5.2.

Tanase et al., Oxygen-tension measurements—the first step towards prevention and early detection of anastomotic leakage, Dec. 17, 2007.

Subbaiyan et al., 'Post-operative wireless implants for monitoring, detection and treatment', Transducers 2011, Beijing, China, Jun. 5-9, 2011, pp. 2192-2195 abstract; figure 1; p. 2193 (first paragraph) and p. 2194 1-13, 17-21, 23, 27-39, 43-47, 49 p. 2193 (first paragraph) and p. 2914.

* cited by examiner

SENSING OF GASEOUS LEAKAGE INTO BODY FOR EARLY DETECTION OF COLORECTAL ANASTOMOTIC LEAKAGE

CROSS-REFERENCE TO RELATED APPLICATION

This Application is the National Stage filing under 35 U.S.C. §371 of PCT Application Ser. No. PCT/US2012/035632 filed on Apr. 27, 2012. The disclosure of the PCT Application is herein incorporated by reference in its entirety.

BACKGROUND

Unless otherwise indicated herein, the materials described in this section are not prior art to the claims in this application and are not admitted to be prior art by inclusion in this section.

During colorectal surgery, a portion of the colon may be removed and the two remaining ends of the colon may be reattached together (or anastomosed). The location of the sutures and/or staple line, where the remaining ends of the colon are joined together is referred to as the anastomosis. Anastomotic leakage is a common complication after colorectal surgery, and may occur at the location of the anastomosis, during which gases and/or fluids may leak from inside of the colon into the intraperitoneal space of the abdominal cavity which can cause severe illness and even death. The anastomotic leakage can occur post-operatively as the body resumes gas production and the internal pressure within the colon increases and puts pressure on the anastomosis allowing gas and/or fluids to leak into the intraperitoneal space at the anastomosis location. Often times, the initial leakage may go undetected until severe symptoms including peritonitis, abscess, sepsis, and even death occur. Early detection of anastomotic leakage after surgery is important for enabling early intervention and management of the anastomosis in order to avoid severe complications, illness, and death due to the leakage.

SUMMARY

The present disclosure generally describes techniques for detecting the presence of gas in the intraperitoneal space of the abdominal cavity and indicating anastomotic leakage. According to some embodiments, the present disclosure describes a method for detecting presence of a gaseous leakage inside a body. The method for detecting presence of a gaseous leakage inside a body may include positioning a sensing device in an abdominal cavity configured to detect a presence of one or more gases, positioning a wireless communication device external to the body configured to receive gas detection information from the sensing device via short-range communication, and determining the gaseous leakage to the abdominal cavity based on the received gas detection information.

According to other embodiments, the present disclosure also describes a system for detecting a gaseous leakage inside a body. The system for detecting a gaseous leakage inside a body may include a sensing device positioned inside the body configured to detect presence of one or more gases, and a wireless communication device positioned external to the body configured to receive gas detection information from the sensing device via short-range communication.

According to further embodiments, the present disclosure describes an intra-body sensing device capable of transmitting information to a wireless communication device for detecting a gaseous leakage inside a body. The sensing device may include at least one sensor configured to detect a leakage of one or more gases at a location of an anastomosis from inside colon into intraperitoneal space based on detected presence of one or more gases in the intraperitoneal space, a transceiver configured to transmit gas detection information to the wireless communication device via short-range communication, a processor, and a power source.

According to yet other embodiments, the present disclosure further describes communication device capable of receiving gas detection information from a sensing device inside a body. The communication device may include a wireless transceiver positioned external to the body.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
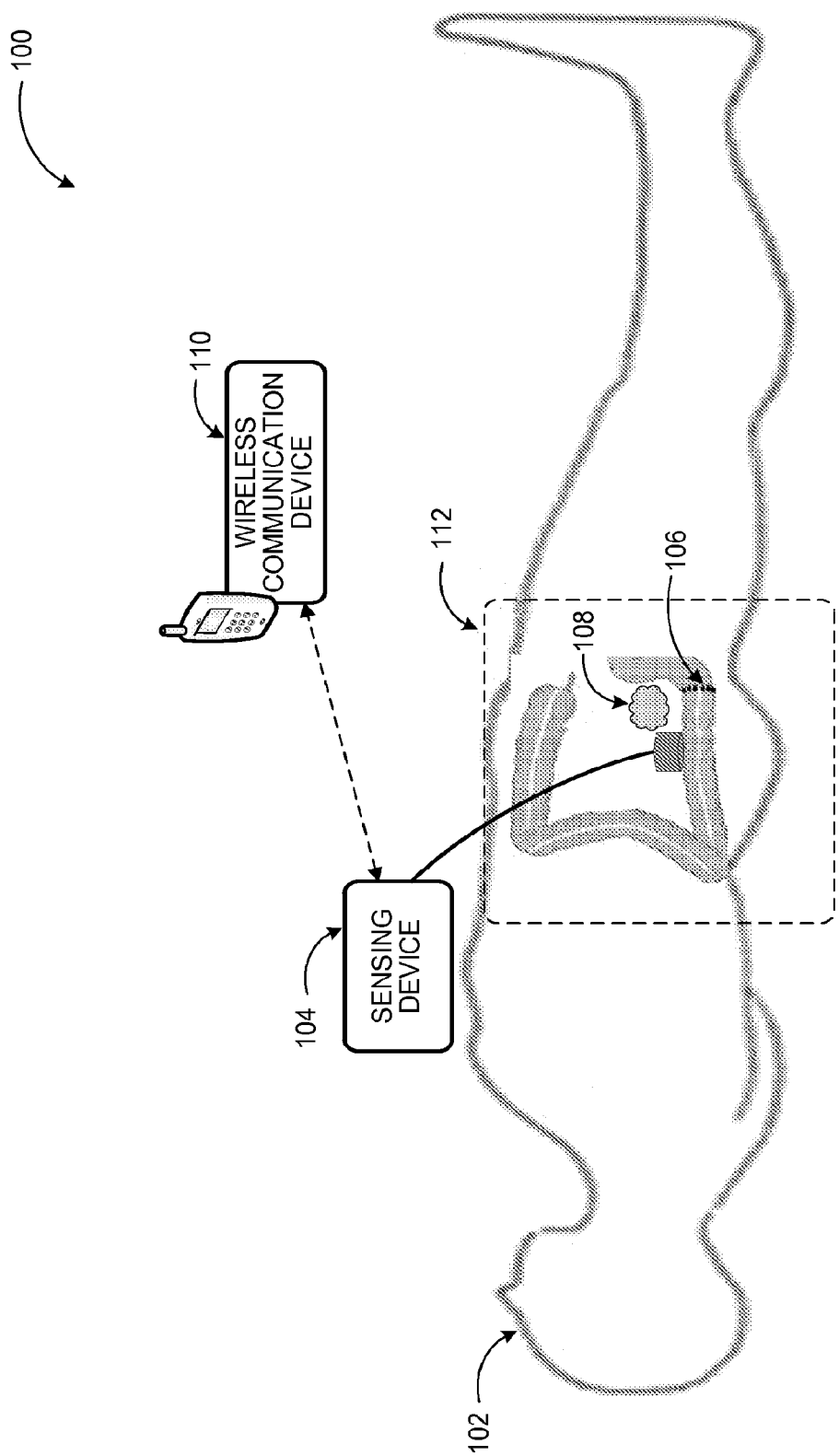
FIG. 1 illustrates an example gas detection system setup, where a sensing device may be placed inside the body and a wireless communication device placed outside the body.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, devices, and/or computer program products related to a gas detection system for detecting the presence of gas inside intraperitoneal space of an abdominal cavity.

Briefly stated, technologies are generally described for a system for detecting the presence of gas in the intraperitoneal space of the abdominal cavity and indicating anastomotic leakage. A sensing device may be implanted inside the abdominal cavity of a body near the location of an anastomosis. The sensing device may utilize a sensor configured to detect gas presence and measure the concentrations of gases, including hydrogen sulfide and/or methane, within the intraperitoneal space. The sensing device may be configured to transmit gas detection information to an external wireless communication device, and the wireless communication device may be configured to generate an alert if a gas concentration level rises above a predetermined acceptable level. The wireless communication device may also be configured to transmit gas detection information to an external monitoring system for performing statistical analysis on the gas detection information for generating more accurate data and more accurately indicating potential anastomotic leakage.

FIG. 1 illustrates an example gas detection system setup, where a sensing device may be placed inside the body and a wireless communication device placed outside the body, arranged in accordance with at least some embodiments described herein. Anastomotic leakage is a common complication after colorectal surgery, during which a portion of the colon is removed. During colorectal surgery, a portion of the colon may be removed and the two remaining ends of the colon may be reattached together (or anastomosed). The location of the sutures and/or staple line where the remaining ends of the colon are joined together is referred to as the anastomosis. After the colorectal surgery, anastomotic leakage may occur at the location of the anastomosis, during which gases and fluids may leak from inside of the colon into the intraperitoneal space of the abdominal cavity which can cause severe illness and even death. The anastomotic leakage can occur post-operatively as a body 102 resumes gas production and the internal pressure within the colon increases and puts pressure on the anastomosis allowing gas and/or fluids to leak into the intraperitoneal space at the anastomosis location. Often times, the initial leakage may go undetected until severe symptoms including peritonitis, abscess, sepsis, and even death occur. Gas leakage typically occurs earlier and faster than fluid leakage, and thus gas detection can provide an early warning of anastomotic leakage. Early detection of anastomotic leakage after surgery is important for enabling early intervention and management of the anastomosis in order to avoid severe complications, illness, and death due to the leakage. Additionally, it is noted that the colon and the gastrointestinal tract is not the only site where an anastomosis can be performed, and it may also be possible to sever and reconnect blood vessels, and to perform similar procedures in the urinary tract (detecting fluids), as some examples.

In a system according to embodiments, a monitoring system as demonstrated in diagram 100 may enable the early detection of anastomotic leakage from the colon into intraperitoneal space 112 of the abdominal cavity by detecting the presence of gases 108 within the intraperitoneal space 112. The monitoring system may be configured to detect gases 108 commonly produced by the body 102 inside the colon, which may include hydrogen sulfide ($H_2S$), methane ($CH_4$), and acetate as some examples. Gases inside the colon are produced during the fermentation of hydrogen within the large intestine, and the type of gas produced inside the colon typically depends on the pH and the presence of various bacteria within the body 102. Hydrogen sulfide and/or methane are the most common gases produced by the fermentation of hydrogen inside the colon, and may typically be produced in a concentration of about 1-10 parts per million.

The monitoring system may include a sensing device 104, which may be placed inside the abdominal cavity within the intraperitoneal space 112 near the location of an anastomosis 106. The sensing device 104 may be configured to detect the presence of small concentrations of gases 108, so that when a small amount of one or more of the gases 108 leak from the colon into the intraperitoneal space 112 through the anastomosis 106, the presence and concentration of the gases 108 may be detected by the sensing device 104. The sensing device 104 may be configured to detect the presence of gas in a sensitivity range of approximately parts per billion, such that when gases such as hydrogen sulfide and/or methane having a concentration in the parts per million range leak in the intraperitoneal space 112 through the anastomosis 106, the sensing device 104 may quickly detect their presence, and may also determine their concentrations.

In an example embodiment, the sensing device 104 may be configured to continuously monitor the intraperitoneal space 112 near the anastomosis 106 for detecting the presence of the gases 108, including hydrogen sulfide and/or methane, inside the intraperitoneal space 112. The sensing device 104 may record the detected concentrations of the hydrogen sulfide and/or methane over time, and may transmit the gas detection information to an external wireless communication device 110. The external wireless communication device 110 may be a wireless communication device, such as a smart phone, Bluetooth device, tablet, RFID reader, a tablet computer, a portable special purpose medical device, and a stationary special purpose medical device, or other similar wireless communication device configured to communicate with the sensing device 104 inside the body 102 via short-range wireless communication. The wireless communication device 110 may be configured to generate an alert if the detected gas concentration levels rise over a predetermined acceptable level, indicating a potential anastomotic leakage. Such a monitoring scenario may enable non-invasive, long-term and continuous monitoring of the intraperitoneal space 112 for early detection of the formation of an anastomotic leakage.

Figure 2:
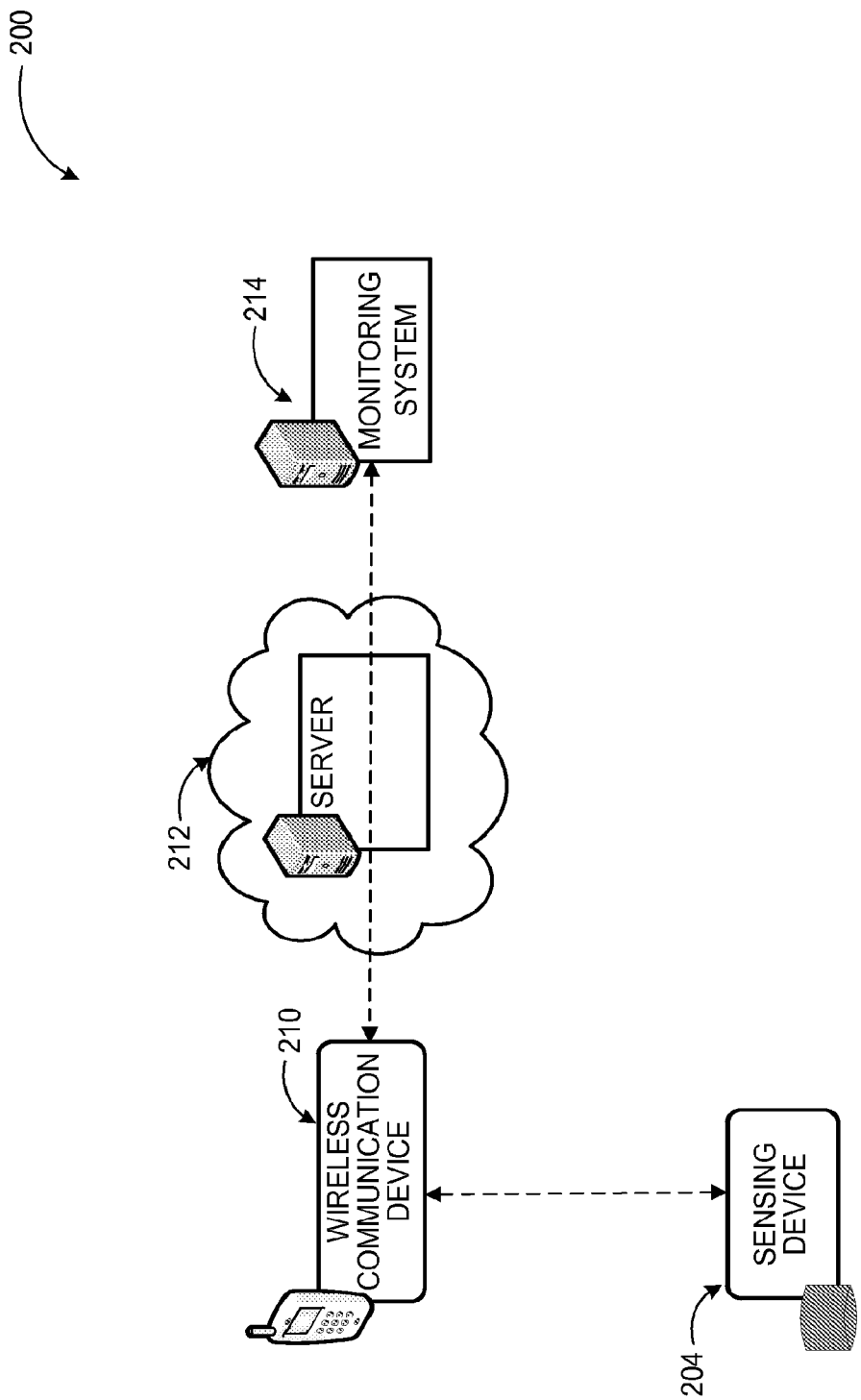
FIG. 2 illustrates an example gas detection setup, where a sensing device may be placed inside the body and communicate with a wireless communication device and a monitoring system placed outside the body.

FIG. 2 illustrates an example gas detection setup, where a sensing device may be placed inside the body and communicate with a wireless communication device and a monitoring system placed outside the body, arranged in accordance with at least some embodiments described herein. In a configuration in a diagram 200, a monitoring system 214 may enable the early detection of anastomotic leakage from the colon into intraperitoneal space of the abdominal cavity by detecting the presence of gases within the intraperitoneal space. The monitoring system may include a sensing device 204, which may be placed inside the abdominal cavity within the intraperitoneal space near the location of an anastomosis. The sensing device may be implanted in the peritoneum lining the abdominal cavity using biologic glue and/or sutures or other similar attachment method.

In an example embodiment, the sensing device 204 may be configured to detect the presence of small concentrations of gases, such as hydrogen sulfide and/or methane, such that if there is an anastomotic leakage, when a small amount of one or more of the gases leaks into the intraperitoneal space through the anastomosis, the presence and concentration of the gases may be detected by the sensing device 204. The sensing device 204 may record the detected concentrations of the hydrogen sulfide and/or methane over time, and may transmit the collected gas detection information to an external wireless communication device 210 positioned external to the body. The sensing device 204 may be able to detect a rate of rise of the gas concentration. Thereby, the sensing device 204 or the external monitoring system 214 may be able to compute the severity of the leak and the necessity of emergent attention. The external wireless communication device 210 may be a wireless communication device configured to communicate via short-range wireless communication with the sensing device 204 inside the body. The external wireless communication device 210 may also be configured to communicate with the external monitoring system 214, through a wireless or wired connection over a network or server 212 for providing the gas detection information to the monitoring system 214.

In a system according to embodiments, the sensing device 204 may include a sensor, a transceiver, a microcontroller, and a power source. The sensor may be configured to primarily detect the presence and concentration of hydrogen sulfide and/or methane. The sensor may be configured to detect the hydrogen sulfide and/or methane in the intraperitoneal space in a sensitivity range of about one part per billion to about one hundred parts per billion. Additionally, in an example embodiment, the sensor may be configured to require low power supply so that it can monitor the anastomosis leakage for long periods of time without requiring to be recharged or replaced, and thus minimizing trips to the doctor for invasive replacement procedure, for example.

An example sensor requiring a low power supply may be a chemically sensitive field effect transistor (ChemFET), which may be chemically configured to detect the presence of hydrogen sulfide ($H_2S$) and methane ($CH_4$). The chemically sensitive field effect transistor acts as a chemical sensor, where the gate electrode can be replaced by a chemically selective material that can, for example, react with a target analyte and convey ions through an electrolyte or membrane to form a gate region, resulting in an analyte controlled resistance that is very low power. The gas sensitivity and selectivity of the ChemFET sensor can be adjusted by surface layers applied by a chemical process in order to make the sensor sensitive to selected gases, such as methane and/or hydrogen sulfide in the parts per billion range.

In another embodiment, the sensor may be composed of a material that is narrowly selective in sensing particular types of gases, such as Tungsten Trioxide ($WO_3$), for example. Tungsten Trioxide is a material that has been shown to be stable, sensitive, and largely selective to hydrogen sulfide gas and methane gas in small quantities. In a system according to embodiments, the sensing device may employ a sensor composed of Tungsten Trioxide for detecting the presence of hydrogen sulfide and/or methane in the intraperitoneal space in the parts per billion sensitivity range.

In a further embodiment, a Tungsten Trioxide sensor may be employed in combination with one or more ChemFET sensors in order to increase the sensitivity and specificity in detecting hydrogen sulfide and/or methane within the intraperitoneal space. Since other ambient gases may be present and detected within the intraperitoneal space, multiple sensors may be used to differentiate the detected gases and to specifically identify the presence of hydrogen sulfide and/or methane and to determine their relative concentrations. Using multiple sensors of any type together, the monitoring system can combine their readings and build an algorithmic method to enhance distinguishing hydrogen sulfide and/or methane from other detected ambient gases. This may be performed at the sensor as well. In some embodiments, the sensor may need to be pulsed to a particular temperature for increasing the sensitivity during measurement. The power source within the sensing device may be employed for providing power to periodically heat the sensor for enabling sampling and gas detection.

In another example embodiment, the sensing device may be coated in a polymer for providing a hydrophobic surface for protecting the sensor from bodily fluids present within the intraperitoneal space. The polymer coating may allow the transportation of one or more gases, such as hydrogen sulfide and/or methane through the polymer to reach the sensor in the sensing device. An example polymer may be a silicone-based organic polymer, which may be configured to be permeable to hydrogen sulfide ($H_2S$) and methane ($CH_4$).

In a further embodiment, the sensing device may include a sensor coupled to a Radio Frequency Identification (RFID) tag. The RFID tag may be a passive tag configured to provide power to the sensor for monitoring and detecting the presence of hydrogen sulfide and/or methane near the anastomosis. In another embodiment, the RFID tag may be an active tag for interacting with the sensor to detect the presence and concentration of methane and/or hydrogen sulfide near the anastomosis and processing and storing the gas detection information. When the RFID tag is an active tag, the sensing device may also include an additional power source for providing the RFID tag and the sensor with power for detecting the presence and concentration of methane and/or hydrogen sulfide near the anastomosis. Additionally, an RFID reader may be positioned outside of the body as an example wireless communication device for receiving gas detection information from the sensor and the RFID tag. The RFID reader may be configured to activate the RFID tag for enabling the RFID tag to transmit the gas detection information detected by the sensor to the RFID reader.

In a system according to embodiments, the wireless communication device 210 may transmit the gas detection information received from the sensor within the sensing device 204 to the monitoring system 214 for collecting, storing, and analyzing the gas detection information. The sensing device 204 may be configured to periodically sample the intraperitoneal space near the anastomosis to measure the concentration of detected gases over a period of time. For example, the sensor may be configured to sample the intraperitoneal space every two minutes such that gas detection data is collected 720 times a day. The sensing device 204 may transmit the gas detection data to the wireless communication device 210 after each sampling or at predetermined intervals. The wireless communication device 210 may be configured to generate an alert if the gas detection data indicates that a concentration of detected gases exceeds a predetermined threshold concentration level, which may indicate an anastomotic leakage.

In another embodiment, the wireless communication device 210 may also transmit the gas detection information to the monitoring system for more in depth analysis of the gas detection data. The monitoring system 214 may apply statistical analysis to the collected gas detection information for determining the amount of gas leaked from an anastomosis into the intraperitoneal space and identifying anastomotic leakage. The statistical analysis of the collected gas detection information may be important as the patient is not a static environment and dietary and other bodily factors can increase the amount of gas produced within the colon. For example, an increase in concentration levels of gas detected in the intraperitoneal space near the anastomosis may not indicate an increased anastomotic leak, but instead may be a result of a temporary increase in gas production within the colon due to dietary changes, medicine(s) the patient takes, or other environmental factors. The statistical analysis can then be applied to analyze gas detection information over time to generate more accurate data for the concentration levels of gases detected within the intraperitoneal space near the anastomosis and more accurately indicate a potential anastomotic leakage. The statistical analysis may also include the use of multiple sensor elements to discriminate particular target gases.

In an example embodiment, the monitoring system 214 may perform an initial calibration to determine a baseline amount of detected gas levels inside an intraperitoneal space. Typically, there may be a small acceptable amount of gas present in the intraperitoneal space, which may not indicate the presence of a significant or threatening anastomotic leak. The monitoring system 214 may recognize that a small amount of gas is acceptable, and gas levels detected at or below the predetermined acceptable amount may not indicate the presence of an anastomotic leak. During an initial calibration, the monitoring system 214 may configure the sensing device 204 to measure the presence and concentration levels of gases within the intraperitoneal space over a predetermined period of time, and the monitoring system 214 may analyze the gas detection data collected over the period of time to determine a baseline acceptable amount of gas.

The monitoring system 214 may also determine a threshold level of gas concentration, which may be a gas concentration level over the predetermined baseline level. The monitoring system 214 may be configured to generate an alert if an amount of gas leaked into the intraperitoneal space rises above the threshold level or rate of change of gas concentration. The alert may be generated by the monitoring system 214 when the gas detection information is transmitted over the server 212 from the sensing device 204 and the wireless communication device 210 and analyzed by the monitoring system 214. Further, the wireless communication device 210 may be configured to automatically generate an alert when it receives gas detection information from the sensing device 204 if the received gas detection information indicates that a detected concentration level or rate of change of gas, including hydrogen sulfide and/or methane, is above the predetermined acceptable concentration level. The threshold level may be initially set at a predetermined gas concentration level by the monitoring system 214. Additionally, the threshold level may be determined based on data collected over a period of time, such that if the detected concentration of one or more gases exceeds a predetermined concentration level for a specified duration, then an alert may be generated by the wireless communication device 210, and/or by the monitoring system 214.

In another embodiment, the predetermined threshold level may be a moving average concentration level based on dietary and bodily factors known to increase gas production by the colon, so that the moving average threshold level may take into consideration changing dietary and environmental influences on gas concentration levels. The moving average threshold may eliminate dietary impact on ambient gas levels within the colon. Further, the monitoring system 214 may be configured to periodically and continuously collect the gas detection information from the wireless communication device 210 in order to continuously update an acceptable amount of gas leakage into the intraperitoneal space based on the gas detection information collected over time. For example, rise over a particular timespan or time of day may be more likely to be dietary and may merit further observation but not intervention. Leakage that stays high may trigger medical follow up while the data may not trigger an alarm if the detected gas returns to lower rates or amounts within a period of time.

Figure 3:
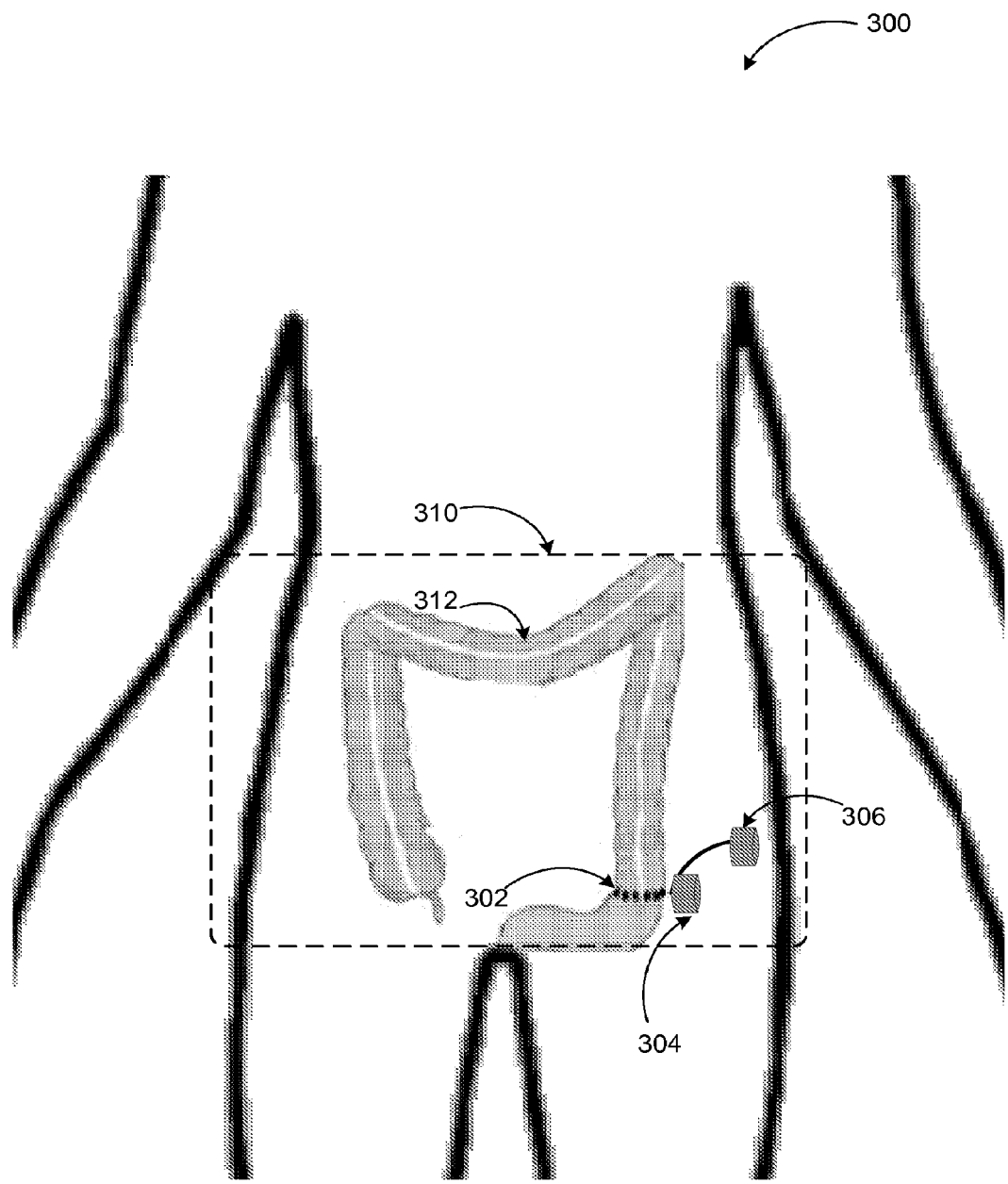
FIG. 3 illustrates an example sensing device placement near an anastomosis inside the body.

FIG. 3 illustrates an example sensing device placement near an anastomosis inside the body, arranged in accordance with at least some embodiments described herein. In a system 300 according to embodiments, a sensing device 304 may be placed inside the abdominal cavity within the intraperitoneal space 310 near the location of an anastomosis 302 for enabling the early detection of anastomotic leakage from the colon 312 into intraperitoneal space 310 of the abdominal cavity by detecting the presence of gases, including hydrogen sulfide and/or methane, within the intraperitoneal space.

In an example embodiment, the sensing device 304 may be configured to detect the presence of small concentrations of gases, such as hydrogen sulfide and/or methane, so that when a small amount of one or more of the gases leaks from the colon 312 into the intraperitoneal space 310 through the anastomosis 302, the presence and concentration of the gases may be detected by the sensing device 304. An example sensing device 304 may include a sensor, a transceiver, a microcontroller, and a power source. The sensing device 304 may be implanted in the peritoneum tissue which lines the abdominal cavity near the anastomosis 302 location using biologic glue and/or sutures or other biological securing methods.

The sensing device 304 may be configured to require low power so that it can monitor the anastomosis leakage for long periods of time with substantially small amounts power from a power source. The power source may be a small power source 306 which may be implanted within the body and connected to the sensing device 304. The power source 306 may be coupled to the sensing device 304 for supplying the sensing device 304 with the power needed to periodically sample the intraperitoneal space 310 for the presence of gas. The power source 306 may be implanted in subcutaneous tissue near the abdominal cavity, and the power source 306 may be attached to the sensing device 304 by a lead. In an example embodiment the power source 306 may be a battery such as a lithium battery or a Nickel-Cadmium battery. The battery may be easily and non-invasively rechargeable such that the sensing device may be able to continuously detect gas concentration levels for long periods of time without having to invasively remove and replace the sensing device and accompanying power source.

In an example scenario of a low power sensing device, the sensing device 304 may utilize nanopower wireless sensor nodes, which utilize nanopower circuitry and pulsed periodic gas concentration checking to preserve the power source. An example nanopower wireless sensor node may use 4 uJ for sampling the gas concentration and 100 nJ for storage of the gas detection information. If the sensing device 304 is configured to sample the gas concentration every two minutes such that gas detection data is collected 720 times a day, then using an example lithium battery power source would enable a power budget for the sensing device 304 of 100 years. Additional power may be required for transmission of the gas detection information from the sensing device to the external wireless communication device, such that the power budget may be reduced to a smaller number of years. A rechargeable battery and/or an easily replaced power source may make it possible for the sensing device to last through multiple years of gas detection before requiring a recharge and/or replacement.

Figure 4:
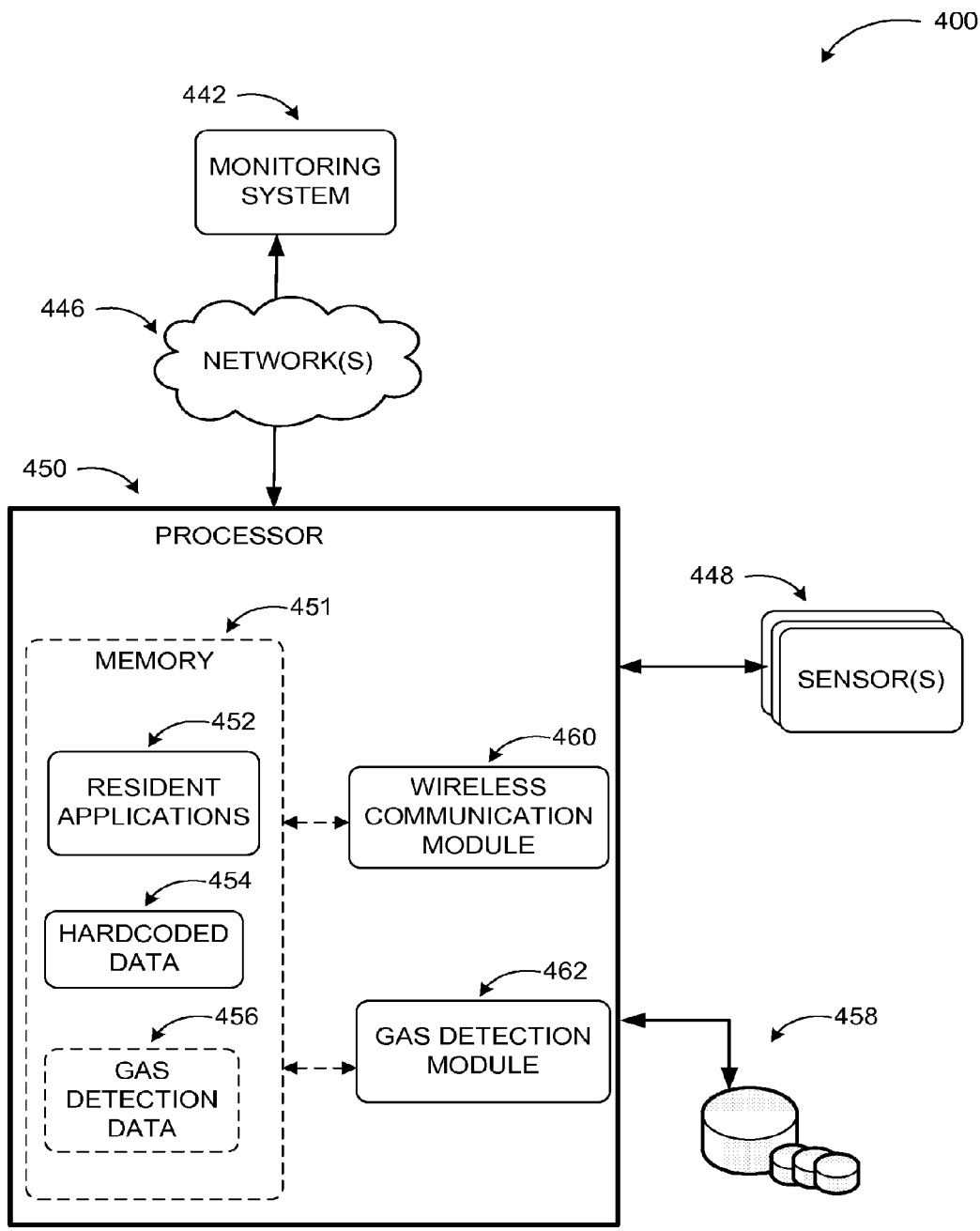
FIG. 4 illustrates a special purpose controller, which may be used to control a sensing device for gas detection placed inside the body.

FIG. 4 illustrates a special purpose controller, which may be used to control a sensing device for gas detection placed inside the body, arranged in accordance with at least some embodiments described herein. According to some embodiments, a gas detection system may be implemented as a special purpose device with a processor 450 and one or more components such as sensor(s) 448. Processor 450 may include special modules such as wireless communication module 460 and gas detection module 462. These modules may employ data acquisition including, but not limited to, gas detection data 456 from inside the body, which may be stored in memory 451 or according to other embodiments in remote data stores 458. The processor 450 may store in its memory 451 resident applications 452, hardcoded data 454, and/or collected gas detection data 456. The resident applications 452 may be any applications that may be executed as part of a functionality of the gas detection system. The hardcoded data 454 may be information stored in a non-volatile memory of the scalable networked device such as definition of the device's functionality, capabilities, identification, etc. In example scenarios, where the gas detection system may collect data from its environment (e.g., a sensor 448), such data may be stored in the memory 451 as well. The processor 450 may further include a wireless communication module 460 for communicating with the components of the gas detection system and wireless communication devices associated with the gas detection system.

Processor 450 may be configured to interact with external monitoring system 442 through operable coupling (wired or wireless) or through network 446. The communications may also be established over the same network(s). By executing instructions for its special modules, processor 450 may control operational parameters of the gas detection system 400 operable coupling (wired or wireless) or through network 446.

Figure 5:
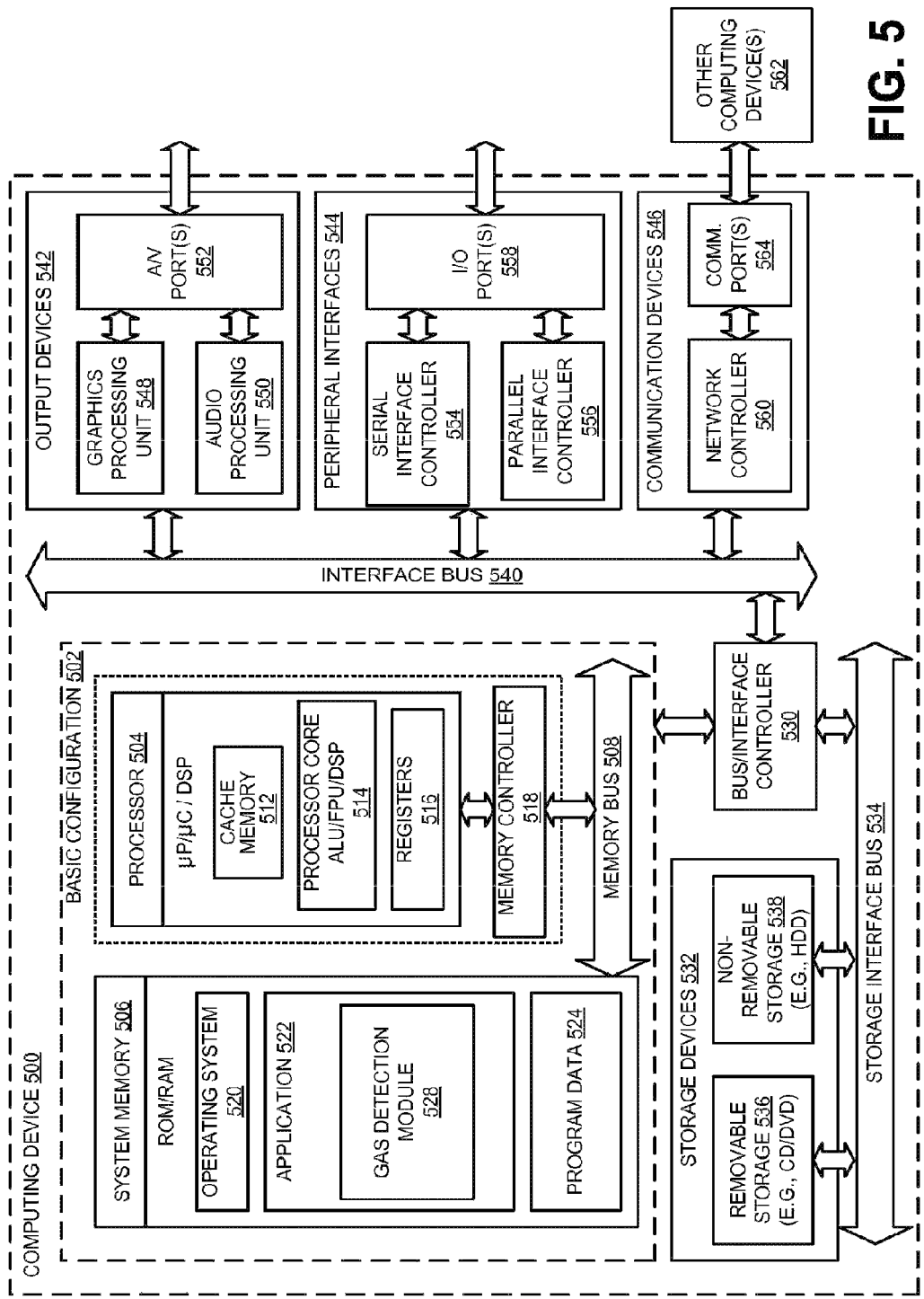
FIG. 5 illustrates a general purpose computing device, which may be used to control a gas detection system implementing a sensing device inside the body and a wireless communication device outside the body.

FIG. 5 illustrates a general purpose computing device, which may be used to control a gas detection system implementing a sensing device inside the body and a wireless communication device outside the body, arranged in accordance with at least some embodiments described herein. In a very basic configuration 502, computing device 500 typically includes one or more processors 504 and a system memory 506. A memory bus 508 may be used for communicating between processor 504 and system memory 506.

Depending on the desired configuration, processor 504 may be of any type including but not limited to a microprocessor (μP), a microcontroller (μC), a digital signal processor (DSP), or any combination thereof. Processor 504 may include one more levels of caching, such as a cache memory 512, a processor core 514, and registers 516. Example processor core 514 may include an arithmetic logic unit (ALU), a floating point unit (FPU), a digital signal processing core (DSP Core), or any combination thereof. An example memory controller 518 may also be used with processor 504, or in some implementations memory controller 518 may be an internal part of processor 504.

Depending on the desired configuration, system memory 506 may be of any type including but not limited to volatile memory (such as RAM), non-volatile memory (such as ROM, flash memory, etc.) or any combination thereof. System memory 506 may include an operating system 520, one or more applications 522, and program data 524. Application 522 may include a gas detection module 528 that is arranged to detect gas levels within the intraperitoneal space and to communicate the detected gas level data to an external monitoring system. Program data 524 may include one or more of gas detection data, and similar data as discussed above in conjunction with FIG. 4. This data may be useful in determining the gaseous leakage to the intraperitoneal space of the abdominal cavity from an anastomosis. In some embodiments, application 522 may be arranged to operate with program data 524 on operating system 520 such that gas detection data is analyzed to generate alerts when gaseous leakage reaches certain levels as described herein. This described basic configuration 502 is illustrated in FIG. 5 by those components within the inner dashed line.

Computing device 500 may have additional features or functionality, and additional interfaces to facilitate communications between basic configuration 502 and any required devices and interfaces. For example, a bus/interface controller 530 may be used to facilitate communications between basic configuration 502 and one or more data storage devices 532 via a storage interface bus 534. Data storage devices 532 may be removable storage devices 536, non-removable storage devices 538, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 506, removable storage devices 536 and non-removable storage devices 538 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 500. Any such computer storage media may be part of computing device 500.

Computing device 500 may also include an interface bus 540 for facilitating communication from various interface devices (e.g., output devices 542, peripheral interfaces 544, and communication devices 546) to basic configuration 502 via bus/interface controller 530. Example output devices 542 include a graphics processing unit 548 and an audio processing unit 550, which may be configured to communicate to various external devices such as a display or speakers via one or more A/V ports 552. Example peripheral interfaces 544 include a serial interface controller 554 or a parallel interface controller 556, which may be configured to communicate with external devices such as input devices (e.g., keyboard, mouse, pen, voice input device, touch input device, etc.) or other peripheral devices (e.g., printer, scanner, etc.) via one or more I/O ports 558. An example communication device 546 includes a network controller 560, which may be arranged to facilitate communications with one or more other computing devices 562 over a network communication link via one or more communication ports 564.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 500 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 500 may also be implemented as a personal computer including both laptop computer and non-laptop computer configurations. Moreover computing device 500 may be implemented as a networked system or as part of a general purpose or specialized server.

Example embodiments may also include methods. These methods can be implemented in any number of ways, including the structures described herein. One such way is by machine operations, of devices of the type described in the present disclosure. Another optional way is for one or more of the individual operations of the methods to be performed in conjunction with one or more human operators performing some of the operations while other operations are performed by machines. These human operators need not be collocated with each other, but each can be only with a machine that performs a portion of the program. In other examples, the human interaction can be automated such as by pre-selected criteria that are machine automated.

Figure 6:
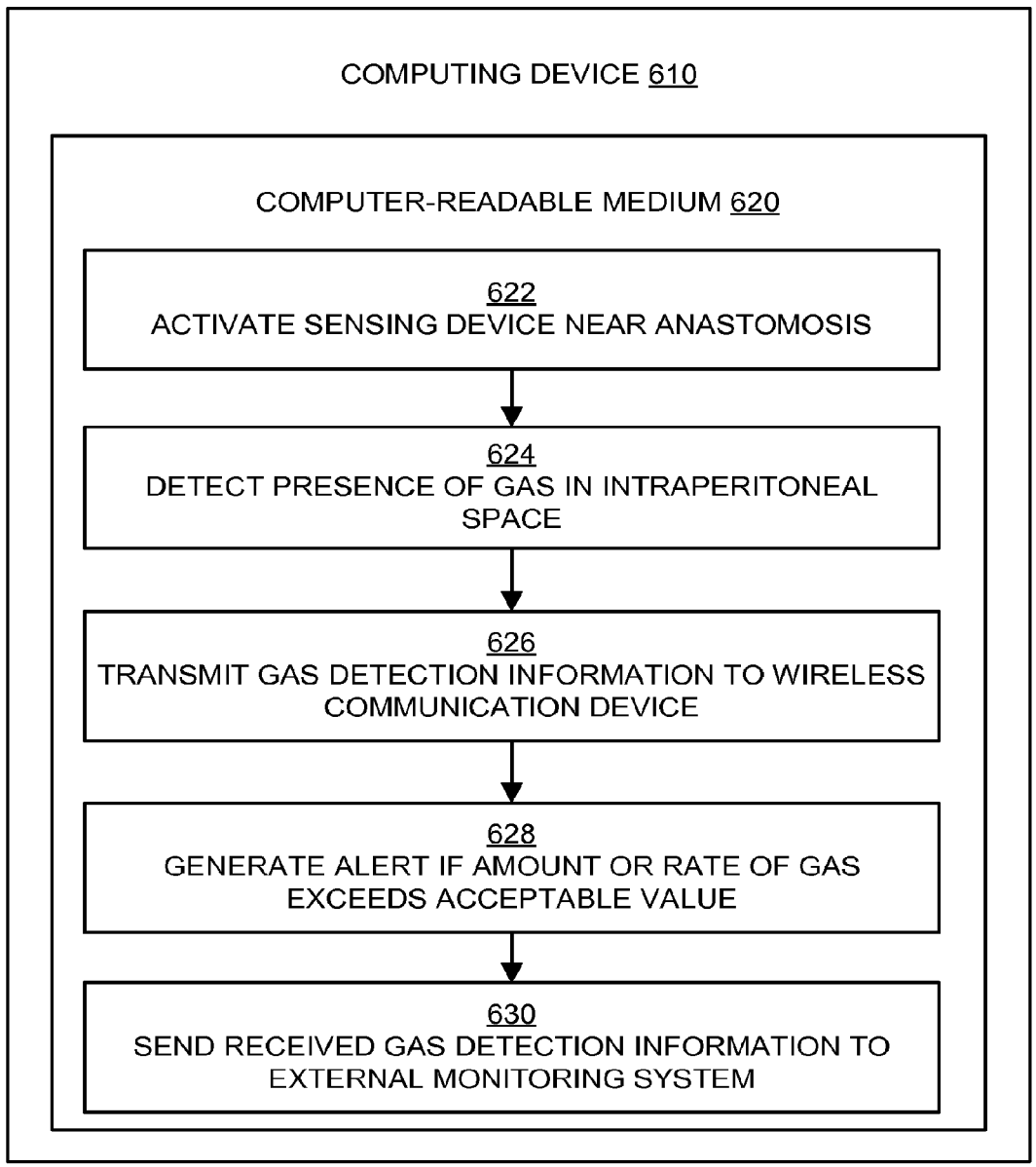
FIG. 6 is a flow diagram illustrating an example method that may be performed by a computing device such as computing device 500 in FIG. 5.

FIG. 6 is a flow diagram illustrating an example method that may be performed by a computing device such as computing device 500 in FIG. 5, arranged in accordance with at least some embodiments described herein. Example methods may include one or more operations, functions or actions as illustrated by one or more of blocks 622, 624, 626, 628 and/or 630. The operations described in blocks 622 through 630 may also be stored as computer-executable instructions in a computer-readable medium such as computer-readable medium 620 of computing device 610.

A process for detecting the presence of gas in the intraperitoneal space of the abdominal cavity and indicating anastomotic leakage may begin with block 622, "ACTIVATE SENSING DEVICE NEAR ANASTOMOSIS". At block 622, a sensing device may be implanted in the peritoneum tissue within the intraperitoneal space near an anastomosis of the colon. The sensing device may include a sensor, power supply, transceiver, and microcontroller. The sensor may be configured to detect the presence of gases, including hydrogen sulfide and/or methane, within the intraperitoneal space.

Block 622 may be followed by block 624, "DETECT PRESENCE OF GAS IN INTRAPERITONEAL SPACE." At block 624, the sensor may periodically and continuously sample the intraperitoneal space for detecting the presence of gases, including hydrogen sulfide and/or methane. The sensor may determine the concentration of the detected gases and may store the gas detection data using a microcontroller within the sensing device.

Block 624 may be followed by block 626, "TRANSMIT GAS DETECTION INFORMATION TO WIRELESS COMMUNICATION DEVICE." At block 626, the sensing device may transmit the collected gas detection data from the sensor and microcontroller to a wireless communication device positioned external to the body via the transceiver.

Block 626 may be followed by block 628, "GENERATE ALERT IF AMOUNT OR RATE OF GAS EXCEEDS ACCEPTABLE VALUE." At block 628, the wireless communication device may generate an alert if an amount of gas leaked into intraperitoneal space or a rate of leakage rises above a predetermined threshold.

Block 628 may be followed by block 630, "SEND RECEIVED GAS DETECTION INFORMATION TO EXTERNAL MONITORING SYSTEM." At block 628, the wireless communication device may transmit the gas detection information to the external monitoring system for more in depth analysis of the gas detection data. The external monitoring system may apply statistical analysis to the collected gas detection information for determining the amount of gas leaked, and an alert may be generated by the external monitoring system when the gas detection information indicates that a detected concentration level of gas, including hydrogen sulfide and/or methane, is above the predetermined acceptable concentration level.

The blocks 622 through 630 may be performed by a dynamic modeling module of a processor of a first computing device (e.g. processor 504 or graphics processing unit 546 of a computing device 500), and may, on the other hand be performed by a graph matching module of the same processor or another processor on a second computing device coupled to the first computing device through a network. Of course, all blocks may be performed by a single module as well.

The blocks included in the above described process are for illustration purposes. A sensing device implanted inside the abdominal cavity of a body and an external monitoring system for detecting the presence of gas in the intraperitoneal space of the abdominal cavity and indicating anastomotic leakage may be performed by similar processes with fewer or additional blocks. In some examples, the blocks may be performed in a different order. In some other examples, various blocks may be eliminated. In still other examples, various blocks may be divided into additional blocks, or combined together into fewer blocks.

Figure 7:
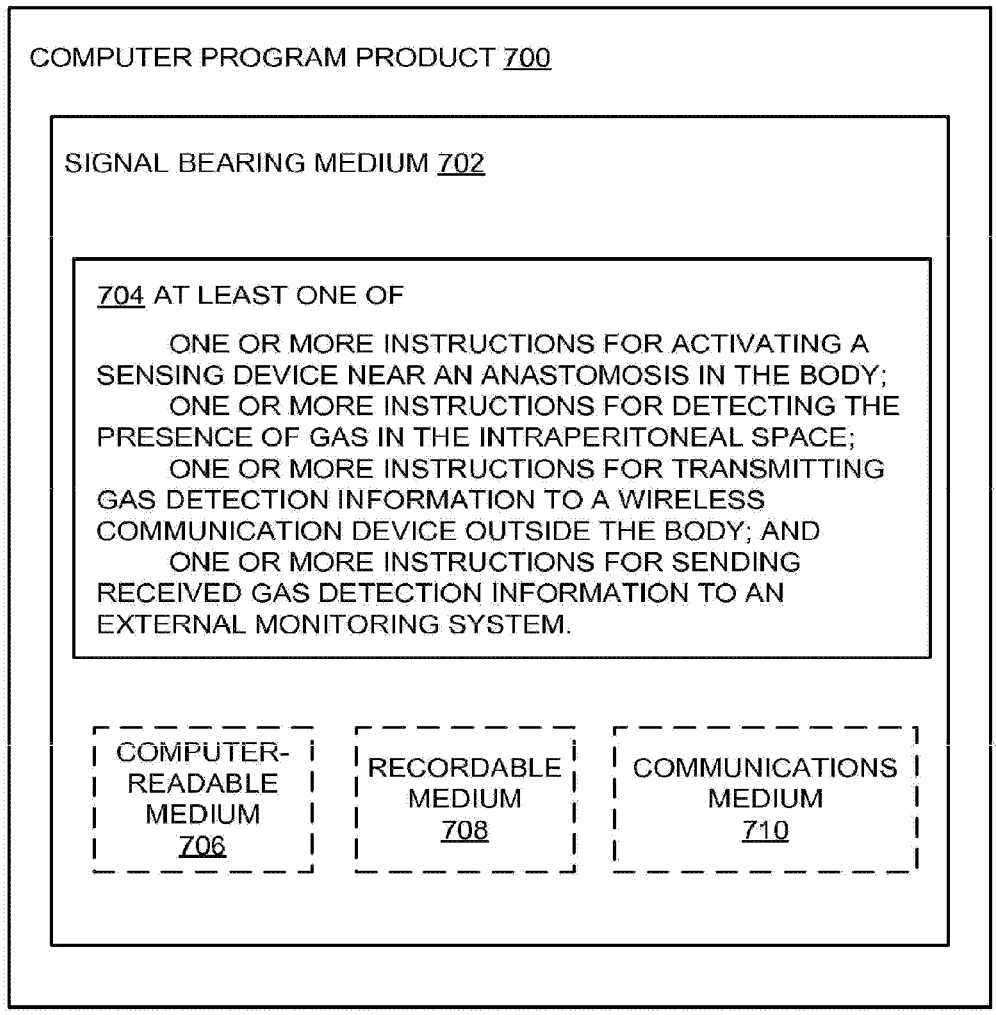
FIG. 7 illustrates a block diagram of an example computer program product, all arranged in accordance with at least some embodiments described herein.

FIG. 7 illustrates a block diagram of an example computer program product, arranged in accordance with at least some embodiments described herein. In some examples, as shown in FIG. 7, computer program product 700 may include a signal bearing medium 702 that may also include machine readable instructions 704 that, when executed by, for example, a processor, may provide the functionality described above with respect to FIG. 4, FIG. 5 and FIG. 6. Thus, for example, referring to processor 504, the gas detection module 528 may undertake one or more of the tasks shown in FIG. 5 in response to instructions 704 conveyed to processor 504 by medium 702 to perform actions associated with detecting the presence of gas in the intraperitoneal space of the abdominal cavity and indicating anastomotic leakage as described herein. Some of those instructions may include activating a sensing device near an anastomosis in the body, detecting the presence of gas in the intraperitoneal space, transmitting gas detection information to a wireless communication device outside the body, and sending received gas detection information to an external monitoring system.

In some implementations, signal bearing medium 702 depicted in FIG. 7 may encompass a computer-readable medium 706, such as, but not limited to, a hard disk drive, a Compact Disc (CD), a Digital Versatile Disk (DVD), a digital tape, memory, etc. In some implementations, signal bearing medium 702 may encompass a recordable medium 708, such as, but not limited to, memory, read/write (R/W) CDs, R/W DVDs, etc. In some implementations, signal bearing medium 702 may encompass a communications medium 710, such as, but not limited to, a digital and/or an analog communication medium (e.g., a fiber optic cable, a waveguide, a wired communications link, a wireless communication link, etc.). Thus, for example, computer program product 700 may be conveyed to one or more modules of the processor 504 by an RF signal bearing medium 702, where the signal bearing medium 702 is conveyed by a wireless communications medium 710 (e.g., a wireless communications medium conforming with the IEEE 802.11 standard).

The present disclosure describes a method for detecting presence of a gaseous leakage inside a body. The method for detecting presence of a gaseous leakage inside a body may include positioning a sensing device in an abdominal cavity configured to detect a presence of one or more gases, positioning a wireless communication device external to the body configured to receive gas detection information from the sensing device via short-range communication, and determining the gaseous leakage to the abdominal cavity based on the received gas detection information.

According to some examples, the sensing device may include: a sensor, a transceiver, a microcontroller, and a power source. The method for detecting presence of a gaseous leakage inside a body may include implanting the power source in subcutaneous tissue, and attaching the power source to the sensor by a lead. The power source may be one of a lithium battery and a Nickel-Cadmium battery. The sensor, the transceiver, the microcontroller, and the power source may be integrated in the sensing device.

According to other examples, the method for detecting presence of a gaseous leakage inside a body may include attaching the sensing device to peritoneum of the abdominal cavity near a location of an anastomosis. The method for detecting presence of a gaseous leakage inside a body may also include detecting a leakage of one or more gases at the anastomosis from inside of colon into intraperitoneal space based on detected presence of one or more gases in the intraperitoneal space. The method for detecting presence of a gaseous leakage inside a body may further include detecting the presence of the one or more gases in the intraperitoneal space in a sensitivity range of about one part per billion to about one hundred parts per billion.

According to further examples, the method for detecting presence of a gaseous leakage inside a body may include attaching the sensing device to peritoneum of the abdominal cavity using one or more of a biologic glue and surgical sutures. The method for detecting presence of a gaseous leakage inside a body may also include employing a sensor in the sensing device to detect one or more of: hydrogen sulfide ($H_2S$) and methane ($CH_4$). The method for detecting presence of a gaseous leakage inside a body may further include employing two or more sensors configured to detect a plurality of gases in the sensing device. The sensing device may include a chemically sensitive field effect transistor configured to detect one or more of: hydrogen sulfide ($H_2S$) and methane ($CH_4$). The sensing device may also include a sensor composed of Tungsten Trioxide ($WO_3$).

According to yet other examples, the method for detecting presence of a gaseous leakage inside a body may include coating the sensing device in a polymer providing a hydrophobic surface for protection against bodily fluids present within intraperitoneal space and permission of transportation of one or more gases to a sensor in the sensing device. The polymer may be a silicon-based organic polymer. The polymer may be configured to be permeable to hydrogen sulfide ($H_2S$) and methane ($CH_4$). The sensing device may include a sensor, a Radio Frequency Identification (RFID) tag, and a microcontroller. The RFID tag may be a passive tag configured to provide power to the sensor. The RFID tag may also be an active tag and the sensing device further comprises a power source.

According to yet further examples, the method for detecting presence of a gaseous leakage inside a body may include positioning an RFID reader outside the body, and enabling the RFID reader to activate the RFID tag for enabling the RFID tag to transmit the gas detection information to the RFID reader. The wireless communication device may be a short range wireless communication device including one of: a Bluetooth device, an RFID reader, a smart phone, a tablet computer, a portable special purpose medical device, and a stationary special purpose medical device. The method for detecting presence of a gaseous leakage inside a body may also include performing a calibration to determine a baseline amount of detected gas inside intraperitoneal space. The method for detecting presence of a gaseous leakage inside a body may further include enabling the wireless communication device to transmit the gas detection information received from the sensing device to an external monitoring system for collecting, storing, and analyzing the gas detection information.

According to some further examples, the method for detecting presence of a gaseous leakage inside a body may include applying statistical analysis to the collected gas detection information for determining an amount of gas leaked from an anastomosis into intraperitoneal space. The method for detecting presence of a gaseous leakage inside a body may include generating an alert if an amount of gas leaked into intraperitoneal space or a rate of gas leakage rises above a predetermined threshold. The method for detecting presence of a gaseous leakage inside a body may also include periodically collecting the gas detection information, and updating an acceptable gas leakage into intraperitoneal space based on the gas detection information collected over a predefined period.

The present disclosure also describes a system for detecting a gaseous leakage inside a body. The system for detecting a gaseous leakage inside a body may include a sensing device positioned inside the body configured to detect presence of one or more gases, and a wireless communication device positioned external to the body configured to receive gas detection information from the sensing device via short-range communication.

The sensing device may include a sensor, a transceiver, a microcontroller, and a power source. The power source may be implanted in subcutaneous tissue and attached to the sensor by a lead. The power source may be one of a lithium battery and a Nickel-Cadmium battery. The sensor, the transceiver, the microcontroller, and the power source may be integrated in the sensing device.

According to other examples, the sensing device may be attached to peritoneum of an abdominal cavity near a location of an anastomosis. The sensing device may be further configured to detect a leakage of one or more gases at the anastomosis from inside of colon into intraperitoneal space based on detected presence of one or more gases in the intraperitoneal space. The presence of the one or more gases in the intraperitoneal space may be detected in a sensitivity range of about one part per billion to about one hundred parts per billion.

According to further examples, the sensing device may be attached to peritoneum of the abdominal cavity using one or more of: a biologic glue and surgical sutures. The sensing device may include a sensor configured to detect one or more of: hydrogen sulfide ($H_2S$) and methane ($CH_4$). The sensing device may include two or more sensors configured to detect a plurality of gases in the sensing device. The sensing device may include a chemically sensitive field effect transistor configured to detect one or more of: hydrogen sulfide ($H_2S$) and methane ($CH_4$). The sensing device may include a sensor composed of Tungsten Trioxide ($WO_3$).

According to yet other examples, the sensing device may be coated in a polymer providing a hydrophobic surface for protection against bodily fluids present within intraperitoneal space and permission of transportation of one or more gases to a sensor in the sensing device. The polymer may be a silicon-based organic polymer. The polymer may be configured to be permeable to hydrogen sulfide ($H_2S$) and methane ($CH_4$). The sensing device may include a sensor, a Radio Frequency Identification (RFID) tag, and a microcontroller. The RFID tag may be a passive tag configured to provide power to the sensor. The RFID tag may be an active tag and the sensing device further comprises a power source.

According to other examples, system for detecting a gaseous leakage inside a body may also include an RFID reader positioned outside the body, the RFID reader enabled to activate the RFID tag for enabling the RFID tag to transmit the gas detection information to the RFID reader. The wireless communication device may be a short range wireless communication device including one of: a Bluetooth device, an RFID reader, a smart phone, a tablet computer, a portable special purpose medical device, and a stationary special purpose medical device. A calibration may be performed to determine a baseline amount of detected gas inside intraperitoneal space. The wireless communication device may be enabled to transmit the gas detection information received from the sensing device to an external monitoring system for collection, storage, and analysis of the gas detection information.

According yet further examples, statistical analysis may be applied to the collected gas detection information to determine an amount of gas leaked from an anastomosis into intraperitoneal space. The wireless communication device may be further configured to generate an alert if an amount of gas leaked into intraperitoneal space or a rate of gas leakage rises above a predetermined threshold. The wireless communication device may be further configured to periodically collect the gas detection information, and update an acceptable gas leakage into intraperitoneal space based on the gas detection information collected over a predefined period.

The present disclosure further describes an intra-body sensing device capable of transmitting information to a wireless communication device for detecting a gaseous leakage inside a body. The sensing device may include at least one sensor configured to detect a leakage of one or more gases at a location of an anastomosis from inside colon into intraperitoneal space based on detected presence of one or more gases in the intraperitoneal space, a transceiver configured to transmit gas detection information to the wireless communication device via short-range communication, a processor, and a power source.

According to some examples, the intra-body sensing device may also include a sensor in the sensing device configured to detect one or more of: hydrogen sulfide ($H_2S$) and methane ($CH_4$). The sensor may include a chemically sensitive field effect transistor configured to detect one or more of: hydrogen sulfide ($H_2S$) and methane ($CH_4$). The sensor may be composed of Tungsten Trioxide ($WO_3$). The sensing device may be coated in a polymer providing a hydrophobic surface for protection against bodily fluids present within intraperitoneal space and permission of transportation of one or more gases to a sensor in the sensing device.

The present disclosure further describes communication device capable of receiving gas detection information from a sensing device inside a body. The communication device may include a wireless transceiver positioned external to the body. The transceiver may be configured to wirelessly receive gas detection information from the sensing device positioned in intraperitoneal space via short-range communication, and to transmit the received gas detection information to a monitoring system. The communication device may include one or more of: a Bluetooth device, an RFID reader, a smart phone, a tablet computer, a portable special purpose medical device, and a stationary special purpose medical device.

According to some examples, the sensing device may be configured to perform an initial calibration to determine a baseline amount of detected gas inside the intraperitoneal space near a location of an anastomosis. The monitoring system may be configured to receive, store, and analyze the gas detection information. The monitoring system may be configured to apply a statistical analysis for determining an amount of gas leaked from an anastomosis into the intraperitoneal space. The communication device may be configured to generate an alert if the amount of gas leaked into the intraperitoneal space or a rate of gas leakage exceeds a predetermined threshold.

There is little distinction left between hardware and software implementations of aspects of systems; the use of hardware or software is generally (but not always, in that in certain contexts the choice between hardware and software may become significant) a design choice representing cost vs. efficiency tradeoffs. There are various vehicles by which processes and/or systems and/or other technologies described herein may be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, a solid state drive, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity of gantry systems; control motors for moving and/or adjusting components and/or quantities).

A typical data processing system may be implemented utilizing any suitable commercially available components, such as those typically found in data computing/communication and/or network computing/communication systems. The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than,"

"less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system to detect a gaseous leakage inside a body, the system comprising:
    a sensing device, wherein the sensing device is configured to be implanted by one or more of biologic glue and sutures in a peritoneum tissue that lines an abdominal cavity near an anastomosis location in the body, and wherein the sensing device is configured to detect a presence of one or more gases in an intraperitoneal space in the body, and generate and transmit gas detection information; and
    an external monitoring system for collection and storage of the gas detection information;
    a wireless communication device configured to be positioned external to the body, wherein the wireless communication device is configured to:
        receive the gas detection information from the sensing device via short-range communication; and
        enable a transmission of the gas detection information received from the sensing device to the external monitoring system; and
    wherein the external monitoring system is configured to:
        apply a statistical analysis to the gas detection information to discriminate between the one or more gases and to determine an amount of gaseous leakage of the one or more gases from an anastomosis into the intraperitoneal space;
        collect the gas detection information; and
        update an acceptable of the gaseous leakage into the intraperitoneal space based on the gas detection information collected over a predefined period.

2. The system of claim 1, wherein the sensing device comprises: a sensor, a transceiver, a microcontroller, and a power source.

3. The system of claim 1, wherein the sensing device includes a chemically sensitive field effect transistor configured to detect one or more of: hydrogen sulfide ($H_2S$) and methane ($CH_4$).

4. The system of claim 1, wherein the sensing device includes a sensor composed of Tungsten Trioxide ($WO_3$).

5. The system of claim 1, wherein the sensing device is coated in a polymer that provides a hydrophobic surface for protection against bodily fluids present within the intraperitoneal space and permission of transportation of the one or more gases to a sensor in the sensing device.

6. The system of claim 5, wherein the polymer is a silicon-based organic polymer.

7. The system of claim 5, wherein the polymer is configured to be permeable to hydrogen sulfide ($H_2S$) and methane ($CH_4$).

8. The system of claim 1, wherein the sensing device comprises: a sensor, a Radio Frequency Identification (RFID) tag, and a microcontroller.

9. An intra-body sensing device configured to transmit information to a wireless communication device and configured to detect a gaseous leakage inside a body, the intra-body sensing device being further configured to be implanted by one or more of biologic glue and sutures in a peritoneum tissue that lines an abdominal cavity near an anastomosis location in the body, the intra-body sensing device comprising:
    at least one sensor configured to detect a leakage of one or more gases at a location of an anastomosis from inside a colon into an intraperitoneal space based on a detected presence of the one or more gases in the intraperitoneal space, wherein the at least one sensor includes one of a Tungsten Trioxide ($WO_3$) device and a chemically sensitive field effect transistor;
    a transceiver configured to transmit gas detection information to the wireless communication device via short-range communication, wherein the transceiver includes a Radio Frequency Identification (RFID) tag
    a processor; and
    a power source.

10. The sensing device of claim 9, wherein the at least one sensor is configured to detect one or more of: hydrogen sulfide ($H_2S$) and methane ($CH_4$).

11. The sensing device of claim 9, wherein the sensing device is coated in a polymer that provides a hydrophobic surface for protection against bodily fluids present within the intraperitoneal space and permission of transportation of the one or more gases to the sensor in the sensing device.

* * * * *